(12) United States Patent
Rátzné Simonek et al.

(10) Patent No.: US 6,469,168 B1
(45) Date of Patent: Oct. 22, 2002

(54) PIPERAZINYLALKYLTHIOPYRIMIDINE DERIVATIVES, PHARMACEUTICAL COMPOSITIONS CONTAINING THE SAME, AND A PROCESS FOR THE PREPARATION OF THE ACTIVE SUBSTANCE

(75) Inventors: Ildikó Rátzné Simonek; Dániel Bózsing; Gábor Németh; Gyula Simig; László Poszávácz, all of Budapest; Iván Jakóczi, Monor; György Lévay, Budakeszi; István Gacsályi, Budapest; Károly Tihanyi, Budapest; János Wellmann, Budapest; András Egyed, Budapest, all of (HU)

(73) Assignee: EGIS Gyógyszergyár Rt., Budapest (HU)

( * ) Notice: Subject to any disclaimer, the term of this patent is extended or adjusted under 35 U.S.C. 154(b) by 0 days.

(21) Appl. No.: 10/009,675
(22) PCT Filed: Jun. 29, 2000
(86) PCT No.: PCT/HU00/00064
§ 371 (c)(1),
(2), (4) Date: Feb. 6, 2002

(87) PCT Pub. No.: WO01/00617
PCT Pub. Date: Jan. 4, 2001

(30) Foreign Application Priority Data

Jun. 29, 1999 (HU) .............................. 9902214
Jun. 6, 2000 (HU) .............................. 0002156

(51) Int. Cl.$^7$ .............................................. C07D 403/00
(52) U.S. Cl. ...................................................... 544/296
(58) Field of Search ......................................... 544/296

(56) References Cited

FOREIGN PATENT DOCUMENTS

WO      WO97/16429      5/1997

Primary Examiner—John M. Ford
(74) Attorney, Agent, or Firm—Heller Ehrman White & MaAuliffe LLP

(57) ABSTRACT

Piperazinylalkylthiopyrimidine derivatives of formula (I), a process for preparing them, and pharmaceutical compositions containing them as active substances. The compounds are useful for the treatment of central nervous system disorders, especially anxiety.

18 Claims, No Drawings

PIPERAZINYLALKYLTHIOPYRIMIDINE DERIVATIVES, PHARMACEUTICAL COMPOSITIONS CONTAINING THE SAME, AND A PROCESS FOR THE PREPARATION OF THE ACTIVE SUBSTANCE

This is a 371 of PCT/HU00/00064, filed Jun. 29, 2000.

The invention refers to novel piperazinylalkylthiopyrimidine derivatives, pharmaceutical compositions containing the same, and a process for the preparation of the active substance. The novel compounds can be employed mainly for the treatment of diseases that form due to disorders of the central nervous system.

More specifically, the invention refers to a novel piperazinylalkylthiopyrimidine derivative of the formula

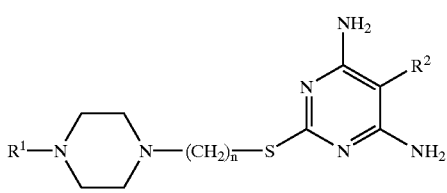

wherein
$R^1$ represents a hydrogen atom, a $C_{1-4}$ alkyl group, a $C_{1-4}$ alkanoyl group or a di($C_{1-4}$ alkyl)amino($C_{1-4}$ alkyl) group,
$R^2$ stands for a hydrogen atom or a benzyl group substituted by 1 to 3 substituent(s) selected from the group consisting of a $C_{1-4}$ alkyl group, a $C_{1-4}$ alkoxy group, a di($C_{1-4}$ alkyl)amino group, a hydroxy group and a halo atom,
n has a value of 2, 3 or 4,
and a pharmaceutically suitable acid addition salt thereof.

From Patent Application WO 97/16429, piperazinylalkylthiopyrimidine derivatives are known wherein the piperazine ring is substituted by a phenyl or a benzyl group at the nitrogen atom in position 4. The known compounds are suitable especially for the treatment of diseases of the central nervous system and have, for example, an outstanding anxiolytic activity. It is an important feature of the known compounds that they exert an effect at the serotonin receptors (5-$HT_{2A}$, 5-$HT_{2C}$). A considerable drawback of the known compounds resides in the fact that the compounds having the best anxiolytic effect metabolize very quickly in the living organism. Thus, the known compounds have a low biological utility that inhibits the development of drugs used in the clinical practice.

The aim of the invention is to prepare novel compounds that are effective mainly within the above field of biological action and more stable than the known compounds from the point of view of metabolism.

It was found that the above aim is achieved by the novel piperazinylalkylthiopyrimidine derivatives of the formula I having anxiolytic activity. However, the novel compounds do not exert any action on the serotonin receptors, and the metabolism thereof is not fast.

In the description, a $C_{1-4}$ alkyl group is a methyl, ethyl, n-propyl, isopropyl, n-butyl, sec.-butyl, tert.-butyl or isobutyl group. Preferably, a $C_{1-4}$ alkyl group is a methyl group or an isopropyl group.

A $C_{1-4}$ alkoxy group is, primarily, a methoxy, ethoxy, n-propoxy or n-butoxy group, preferably a methoxy group.

A halo atom is, in general, a fluoro, chloro or bromo atom, preferably a chloro atom or a fluoro atom.

Under a $C_{1-4}$ alkanoyl group a formyl, acetyl, n-propanoyl, n-butanoyl group etc., preferably an acetyl group is meant.

The pharmaceutically suitable acid addition salts of the compounds of the formula I are the acid addition salts of the compounds formed with pharmaceutically suitable inorganic or organic acids including sulfonic acids. Preferred acid addition salts are the hydrogen halides such as hydrochlorides or hydrobromides, carbonates, hydrogen carbonates, sulfates, phosphates, acetates, fumarates, maleates, citrates, ascorbates and benzenesulfonates.

A preferred subgroup of the compounds of the invention consists of the compounds of the formula I and the pharmaceutically suitable acid addition salts thereof, wherein
$R^1$ represents a hydrogen atom, a dimethylamino($C_{1-4}$ alkyl) group or a $C_{1-4}$ alkanoyl group,
$R^2$ is as defined in connection with formula I,
n has a value of 2 or 3.

The especially preferred piperazinylalkylthiopyrimidine derivatives of the invention consist of the compounds of the formula I, wherein
$R^1$ represents a hydrogen atom or a dimethylamino($C_{1-4}$ alkyl) group,
$R^2$ stands for a benzyl group substituted by a $C_{1-4}$ alkoxy group, or a fluoro atom,
n has a value of 2,
and pharmaceutically suitable acid addition salts thereof.

In the definition of $R^2$, conveniently, the $C_{1-4}$ alkoxy group is in position ortho.

The compounds of the invention are prepared by reacting a 2-mercaptopyrimidine of the formula

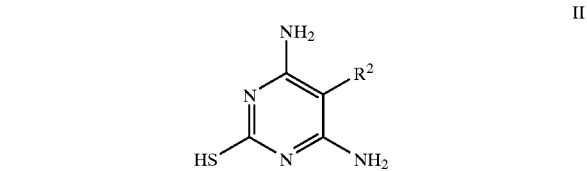

wherein $R^2$ is as defined above, or an alkali metal salt thereof, with a haloalkylpiperazine of the formula

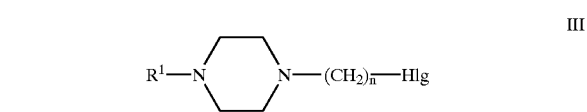

wherein $R^1$ and n are as stated above, Hlg represents a halo atom, preferably a chloro or bromo atom, or an acid addition salt thereof, and, if desired, converting the compound of the formula I to a pharmaceutically suitable acid addition salt thereof, or liberating it from the acid addition salt thereof.

If desired, an obtained compound of the formula I can be transformed into another compound of the formula I. These additional transformations can be performed in a manner known per se. Thus, an obtained compound of the formula I, wherein $R^1$ is a hydrogen atom, can be alkylated to obtain a compound of the formula I, wherein $R^1$ stands for a $C_{1-4}$ alkyl group. Compounds of the formula I, wherein $R^1$ represents a dialkylaminoethyl group or an alkanoyl group, can be prepared through a similar additional transformation (alkylation or acylation). According to a further example of the additional transformation, a compound of the formula I, wherein $R^2$ stands for an alkoxybenzyl group, is prepared by alkylating a compound of the formula I, wherein $R^2$ is a hydroxybenzyl group, or a compound of the formula I, wherein $R^1$ is a hydrogen atom, is prepared from the corresponding compound of the formula I, wherein $R^1$ is a formyl group, and the latter group is removed by hydrolysis.

The process of the invention is carried out in an organic solvent or solvent mixture that is indifferent from the point of view of the reactants. For example, aliphatic alcohols such as methyl alcohol, isopropyl alcohol, dialkylamides, preferably dimethylformamide, water or a mixture thereof can be employed. The reaction of the compounds of the formulae II and III is performed either by using an alkali metal salt of the 2-mercaptopyrimidine of the formula II, or in the presence of an acid binding agent. For this purpose, preferably alkali metal carbonates such as sodium or potassium hydrogen carbonate, alkali metal hydroxides such as sodium or potassium hydroxide, alkali earth metal hydroxides such as calcium hydroxide, or tertiary amines such as pyridine, triethylamine or other trialkylamines can be used.

Preferably, the acid binding agent is potassium hydroxide, potassium carbonate or sodium carbonate.

Optionally, the reaction can be accelerated by means of a catalyst. Primarily, alkali metal halides or alkali earth metal halides (for example, potassium iodide, potassium fluoride, sodium bromide or calcium chloride) are used as the catalyst. Preferably, the reaction is carried out in the presence of potassium iodide catalyst.

The reaction is performed at a temperature between room temperature and the boiling point of the reaction mixture, depending on the reactivity of the starting substances. In an aqueous solution it is preferred to proceed at room temperature, in other cases a reaction temperature from 60 to 80° C. is preferred. The reaction time is 2 to 20 hours, depending on the reactivity of the starting substances and the temperature employed.

The starting compounds of the formulae II and III can be used in an equimolar amount or the haloalkylpiperazine of the formula III is added to the reaction mixture in an excess of 10% at the most. The acid binding agent is used in an equimolar quantity, however, it can be employed even in a tenfold excess. When the starting substance is a salt of the mercapto compound, a lower amount of acid binding agent is needed, in general. Calculated for each mole of the 2-mercaptopyrimidine of the formula II, 0.1 to 0.2 moles of the catalyst is used, in general; preferably the reaction is performed in the presence of 0.1 moles of catalyst.

The reaction mixture is worked up in a manner known per se. It is preferred to separate the product as follows: the solution is separated from the precipitated inorganic salts by filtration, the filtrate is evaporated under reduced pressure, and the residue is crystallized from water or an organic solvent, or the precipitated product and inorganic salts are filtered together, and the inorganic salts are removed by washing with water. According to a further possibility, the reaction mixture is poured onto water to remove the inorganic salts, then the product is extracted or the precipitated product is filtered. If desired, the product is purified by known purification procedures such as recrystallization or chromatography.

The compounds of the formula I can be separated in the form of pharmaceutically suitable acid addition salts mentioned before, or the compounds of the formula I obtained as a base are converted to an acid addition salt by reacting the base in an indifferent solvent with the corresponding acid. From the acid addition salt, the base can be repeatedly liberated, then converted to another acid addition salt.

The starting compounds of the formula II are known from the literature. They can be prepared as described in Patent Application WO 97116429. Haloalkylpiperazines of the formula III are also known, with the exception of the compound, wherein $R^1$ represents an isopropyl group. They can be prepared by the process given in U.S. Pat. No. 2,851,458. The preparation of the halo compound, wherein $R^1$ stands for a formyl group, is described in the article Arzneim. Forsch., 12, 937–942 (1962), and that of the halo compound, wherein $R^1$ means an acetyl group, is described in BE-P 645 602.

The compounds of the formula I have an effect on the central nervous system, and possess an especially valuable psychotropic action.

The biological effect of the compounds of the formula I was proved by the following tests:

1. Elevated Plus-Maze Test

The tests were carried out on male SPRD rats weighing 220 to 260 g. Each group of animal consisted of 8 to 10 pieces of rat. The substance to be examined or the vehicle (i.e. distilled water or a 0.4% solution of methylcellulose) was administered to the animals in a volume of 5 ml/kg as a solution or suspension per os 60 minutes prior to the test.

The elevated plus-maze consists of two open and two 40 cm wall enclosed arms of the same size (50×15 cm) arranged in the shape of a cross. The arms of the same type are opposite to each other. The junction of the four arms forms a central square area (15×15 cm). The apparatus is made of a wooden material elevated to a height of 50 cm and illuminated by a dim light from above. The essence of the method is that during the exploration of the apparatus, the animals spend considerably more time in the closed arms than in the open arms due to the natural fear from open space and height. Compounds having anxiolytic effect can significantly increase the time spent in the open arms as well as the number of entries into the open arms. The average values of these parameters were calculated, and, after statistical analysis, the minimum effective dose was determined for each compound [Pelow, S., Chopin, P., File, S. E., Briley, M.: Validation of open:closed arm entries in an elevated plus-maze as a measure of anxiety in the rat, J. Neurosci. Methods., 14, 149–167 (1985)].

The results obtained are shown in Table I. Diazepam [7-chloro-1,3-dihydro-1-methyl-5-phenyl-2H-1,4-benzodiazepine-2-one] was used as the reference substance.

TABLE I

| Compound (Example No.) | Minimum effective dose in mg/kg p.o. |
|---|---|
| 1 (besylate) | 1 |
| 1 (fumarate) | 3 |
| 2 | 1 |
| 4 | 1 |
| 5 | 3 |
| 6 | 0.03 |
| 7 | <1 |
| 8 | 3 |
| 9 | 3 |
| 10 | 1 |
| 12 | 1 |
| 13 | 1 |
| 14 | 1 |
| 16 | 3 |
| 17 | 1 |
| 18 | 1 |
| 19 | 0.01 |
| 26 | 0.3 |
| diazepam | 1 |

From Table I it can be seen that the compounds of the invention have the same or superior—in some cases by orders of magnitude superior—anxiolytic action than that of diazepam in the test.

2. Determination of the Spontaneous Motor Activity

For the experiments, male NMRI mice weighing 20 to 25 g were used. Each treatment group consisted of 10 mice. The substance to be examined or the vehicle (i.e. a 0.4% solution of methylcellulose) was administered to the animals in a volume of 20 ml/kg as a suspension per os 60 minutes prior to the test. The method gives a general information about the influence of the substance to be examined on the natural motion of animals, thus, the method reveals any sedative effect of the substance. In case of anxiolytics, the value of the anxiolytic effect depends on the presence or absence of the sedative action (the latter is desirable). For the experiments, an apparatus "digital motimeter" having 10 measuring places was used. The motion of the animals was indicated by the interruption of three parallel beams of infrared light at each measuring place, and the interruptions were recorded by the apparatus. The activity of one animal was determined at each measuring place. From the results of the experiments, values of $ID_{50}$ (i.e. the dose producing 50% of inhibition) were calculated [Borsy, I., Csányi, E., Lázár, I., Arch. Int. Pharmacodyn., 124, 180–190 (1960); Stille, G., Leuener, H. and Eichenberger, E., II Farmaco Ed. Pr., 26 603–625 (1971)]. The data obtained are shown in Table II. Diazepam was used as the reference substance.

TABLE II

| Compound (Example No.) | $ID_{50}$ in mg/kg p.o. |
|---|---|
| 1 (besylate) | >90 |
| 1 (fumarate) | >100 |
| 2 | >100 |
| 4 | 32.8 |
| 5 | >100 |
| 6 | >100 |
| 7 | >100 |
| 8 | >100 |
| 16 | >100 |
| 17 | >100 |
| 18 | >100 |
| 19 | >100 |
| 26 | >100 |
| diazepam | 6.9 |

From Table II it can be seen that the compounds of the invention do not influence the motor activity of mice even in a dose that is higher by a factor of 14 than the $ID_{50}$ value of diazepam used as the reference compound.

Summarized, it can be stated that the compounds of the invention have very significant anxiolytic effect, however, no sedative side effect can be observed even in a dose range that is higher by several orders than the anxiolytic dose.

The results of the above examinations suggest that the anxiolytic effect of the novel piperazinylalkylthiopyrimidine derivatives is more favourable than that of the benzodiazepines widely used in the therapy since the latter drugs are characterized by a high sedative side effect.

Thus, the novel piperazinylalkylthiopyrimidine derivatives of the formula I can be used as active ingredients in pharmaceutical compositions.

The pharmaceutical compositions of the invention contain a therapeutically active amount of the compound of the formula I or a pharmaceutically suitable acid addition salt thereof and one or more conventional carrier(s).

The pharmaceutical compositions of the invention are suitable for peroral, parenteral or rectal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinylpyrrolidone) etc.; filling agents such as lactose, glucose, starch, calcium phosphate etc.; auxiliary substances for tabletting such as magnesium stearate, talc, poly(ethylene glycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propylene glycol, ethanol etc.; preservatives such as methyl p-hydroxybenzoate etc. as the carrier.

Pharmaceutical compositions suitable for parenteral administration consist of sterile solutions of the active ingredient, in general.

Dosage forms listed above as well as other dosage forms are known per se, see e.g. Remington's Pharmaceutical Sciences, 18th Edition, Mack Publishing Co., Easton, USA (1990).

The pharmaceutical compositions of the invention contain, in general, 0.1 to 95.0 per cent by mass of a compound of the formula I or a pharmaceutically suitable acid addition salt thereof. A typical dose for adult patients amounts to 0.1 to 1000 mg of the compound of the formula I or a pharmaceutically suitable acid addition salt thereof, daily. The above dose can be administered in one or more portions. The actual dosage depends on many factors and is determined by the doctor.

The pharmaceutical compositions of the invention are prepared by admixing a compound of the formula I or a pharmaceutically suitable acid addition salt thereof to one or more carrier(s), and converting the mixture obtained to a pharmaceutical composition in a manner known per se. Useful methods are known from the literature, e.g. Remington's Pharmaceutical Sciences mentioned above.

Preferably, the pharmaceutical compositions of the invention contain a piperazinylalkylthiopyrimidine derivative of the formula I, wherein $R^1$ represents a hydrogen atom, a dimethylamino($C_{1-4}$ alkyl) group or a $C_{1-4}$ alkanoyl group, $R^2$ is as defined in connection with formula I, n has a value of 2 or 3, or a pharmaceutically suitable acid addition salt thereof as the active ingredient.

The especially preferred pharmaceutical compositions of the invention comprise a piperazinylalkylthiopyrimidine derivative of the formula I, wherein $R^1$ represents a hydrogen atom or a dimethylamino($C_{1-4}$ alkyl) group, $R^2$ stands for a benzyl group substituted by a $C_{1-4}$ alkoxy group or a fluoro atom, n has a value of 2, or a pharmaceutically suitable acid addition salt thereof as the active ingredient.

Furthermore, the invention refers to a method for the treatment of diseases which comprises administering a therapeutically effective non-toxic amount of a piperazinylalkylthiopyrimidine derivative of the formula I or a pharmaceutically suitable acid addition salt thereof to a patient suffering from especially a disease of the central nervous system.

In addition, the invention includes the use of a piperazinylalkylthiopyrimidine derivative of the formula I or a pharmaceutically suitable acid addition salt thereof for the preparation of a pharmaceutical composition having anxiolytic effect.

The invention is further elucidated by means of the following Examples.

EXAMPLE 1

4,6-Diamino-5-(2-methoxybenzyl)-2-[2-(1-piperazinyl)ethylthio]-pyrimidine 5.71 g (19 moles) of 4,6-diamino-2-mercapto-5-(2-methoxy-benzyl)pyrimidine are suspended in a solution of 6.73 g (120 mmoles) of potassium hydroxide in 120 ml of water, and, to the suspension obtained, a solution of 4.43 g (20 mmoles) of 1-(2-chloroethyl)piperazine dihydrochloride in 20 ml of water is added, drop by drop, at 25° C. The reaction mixture is stirred at room temperature for 3 hours, then 140 ml of water and 200 ml of methyl alcohol are added. The mixture is heated to boiling point, then filtered while hot, and the filtrate is allowed to crystallize at 0° C. The substance obtained is purified by chromatography over a column filled with 130 g of Kieselgel 60 and using a mixture of methyl alcohol and toluene in a ratio of 1:1. The product is recrystallized from 100 ml of a mixture of ethyl alcohol and water in a ratio of 1:1, and dried over anhydrous calcium chloride at 80° C. under reduced pressure.

Thus, 4.69 g (60%) of the title compound are obtained.
Formation of the Fumarate Salt 4.64 g (12.4 moles) of the base are suspended in 75 ml of ethyl alcohol. The suspension is heated to boiling, and a solution of 1.47 g (12.6 moles) of fumaric acid in 60 ml of ethyl alcohol is added. After crystallization at room temperature, 6.02 g (99%) of the fumarate salt of the title compound are obtained.

M.p.: 195° C. (under decomposition).

Analysis: for $C_{22}H_{30}N_6O_5S$ (490.59)

calculated: C, 53.86%; H, 6.16%; N, 17.13%; S, 6.54%;
found: C, 53.54%; H, 6.08%; N, 16.97%; S, 6.55%.
Formation of the Besylate Salt 1.0 g (2.67 mmoles) of the base are suspended in 20 ml of ethyl alcohol, and, to the suspension obtained, a solution of 0.42 g (2.67 mmoles) of benzenesulfonic acid in 2 ml of ethyl alcohol are added, drop by drop, at 0° C. The mixture is stirred at room temperature for 5 hours, then filtered. Thus, 1.25 g (88%) of the besylate salt of the title compound are obtained.

M.p.: 173–174° C.

Analysis: for $C_{24}H_{32}N_6O_4S_2$ (532.69)

calculated: C, 54.12%; H, 6.06%, N, 15.78%; S, 12.04%;
found: C, 54.01%; H, 6.15%; N, 15.59%; S, 12.27%.

EXAMPLE 2

4,6-Diamino-5-(2-methoxybenzyl)-2-[2-(1-piperazinyl)ethylthio]-pyrimidine fumarate 2.99 g (9.5 mmoles) of 4,6-diamino-2-mercapto-5-(2-ethoxy-benzyl)pyrimidine are suspended in a solution of 3.37 g (60 mmoles) of potassium hydroxide in 60 ml of water, and, to the suspension obtained, a solution of 2.22 g (10 mmoles) of 1-(2-chloroethyl)piperazine dihydrochloride in 10 ml of water are added, drop by drop, at 25° C. The reaction mixture is stirred at room temperature for 2 hours, then 50 ml of water and 100 ml of methyl alcohol are added. The mixture is heated to boiling point, filtered while hot, and the filtrate is allowed to crystallize at 0° C. The substance obtained is purified by chromatography over a column filled with 130 g of Kieselgel 60 using a mixture of methyl alcohol and toluene in a ratio of 2:3. The crystalline product obtained is recrystallized from a mixture of 20 ml of methyl alcohol and 20 ml of water to obtain 2.20 g of substance that is the dihydrate of the base. This compound is dissolved in 40 ml of ethyl alcohol under heating, and the solution obtained is added to a solution of 0.64 g of fumaric acid in 15 ml of ethyl alcohol. After crystallization at room temperature, 2.56 g (53%) of the title product are obtained. M.p.: 187–189° C.

Analysis: for $C_{23}H_{32}N_6O_5S$ (504.61)

calculated: C, 54.75%; H, 6.39%; N, 16.65%; S, 6.35%;
found: C, 54.72%; H, 6.37%; N, 16.93%; S, 6.33%.

EXAMPLE 3

4,6-Diamino-2-[3-(4-methyl-1-piperazinyl)propylthio]-5-(2-methoxybenzyl)pyrimidine trihydrochloride To a suspension of 6.0 g (20 mmoles) of 4,6-diamino-2-mercapto-5-(2-methoxybenzyl)pyrimidine potassium salt, 2.76 g (20 mmoles) of potassium carbonate and 0.33 g (2 mmoles) of potassium iodide in 100 ml of methyl alcohol, 5.0 g (20 mmoles) of 1-(3-chloropropyl)-4-methylpiperazine dihydrochloride are added, and the reaction mixture is boiled for 20 hours. The mixture is allowed to cool to room temperature, the inorganic salts are filtered, the filtrate is evaporated under reduced pressure, the oil obtained is crystallized from water, the crystalline substance is filtered and dried. The base obtained is reacted in ethyl alcohol with 3 equivalents of hydrogen chloride using isopropanol containing hydrogen chloride.

Thus, 5.5 g (53.7%) of the title product are obtained.

M.p.: above 280° C.

Analysis: for $C_{20}H_{33}Cl_3N_6OS$ (511.95)

calculated: C, 46.92%; H, 6.50%; N, 16.42%; S, 6.26%; Cl, (ionic) 20.78%;
found: C, 46.31%; H, 6.54%; N, 16.14%; S, 6.26%; Cl, (ionic) 20.44%.

EXAMPLE 4

4,6-Diamino-2-[2-(4-methyl-1-piperazinyl)propylthio]-5-(2-methoxybenzyl)pyrimidine trihydrochloride hydrate To a suspension of 6.0 g (20 mmoles) of 4,6-diamino-2-mercapto-5-(2-methoxybenzyl)pyrimidine potassium salt, 5.52 g (40 mmoles) of potassium carbonate and 0.66 g (4 mmoles) of potassium iodide in 50 ml of dimethylformamide, 4.71 g (20 mmoles) of 1-(2-chloroethyl)-4-methylpiperazine dihydrochloride are added, and the reaction mixture is stirred at 80° C. for 10 hours. After cooling, the mixture is poured onto 100 ml of water, the crystals precipitated are filtered and dried. The substance obtained is purified by chromatography over a column filled with Kieselgel 60 using a mixture of methyl alcohol and dichloromethane in a ratio of 1:8. The pure base obtained is reacted in ethyl alcohol with 3 equivalents of hydrogen chloride using isopropanol that contains hydrogen chloride.

Thus, 6.84 g (65.9%) of the title product are obtained.

M.p.: 241–243° C.

Analysis: for $C_{19}H_{33}Cl_3N_6O_2S$ (515.94)

calculated: C, 44.23%; H, 6.45%; N, 16.29%; S, 6.21%; Cl, (ionic) 20.61%;
found: C, 44.32%; H, 6.35%; N, 16.37%; S, 6.22%; Cl, (ionic) 20.92%.

EXAMPLE 5

4,6-Diamino-2-[2-(4-isopropyl-1-piperazinyl) ethylthio]-5-(2-methoxybenzyl)pyrimidine trihydrochloride hydrate A mixture of 6.0 g (20 mmoles) of 4,6-diamino-2-mercapto-5-(2-methoxybenzyl)pyrimidine potassium salt, 5.52 g (40 mmoles) of potassium carbonate, 0.66 g (4 mmoles) of potassium iodide, 5.27 g (20 mmoles) of 1-(2-chloroethyl)-4-isopropylpiperazine dihydrochloride and 150 ml of methyl alcohol are boiled for 20 hours. The reaction mixture is worked up according to the procedure of Example 3, however, the salt formation is carried out from the oil obtained after the evaporation.

Thus, 6.63 g (61.1%) of the title product are obtained.

M.p.: 253–255° C.

Analysis: for $C_{21}H_{37}Cl_3N_6O_2S$ (543.99)

calculated: C, 46.37%; H, 6.86%; N, 15.45%; D, 5.89%; Cl, (ionic) 19.55%;

found: C, 45.98%; H, 6.78%; N, 15.03%; S, 5.76%; Cl, (ionic) 19.61%.

EXAMPLE 6

4,6-Diamino-2-[2-/4-(2-dimethylaminoethyl)-1-piperazinyl/-ethyl-thio]-5-(2-methoxybenzyl) pyrimidine tetrahydrochloride dihydrate A mixture of 1.0 g (3 mmoles) of 4,6-diamino-2-mercapto-5-(2-methoxybenzyl)pyrimidine potassium salt, 1.65 g (12 mmoles) of potassium carbonate, 0.1 g (0.6 mmoles) of potassium iodide, 1.1 g (3 mmoles) of 1-(2-chloroethyl)-4-(2-dimethylamino)ethylpiperazine trihydrochloride hydrate and 20 ml of methyl alcohol is reacted at reflux temperature for 12 hours. The reaction mixture is worked up according to the procedure of Example 4, however, in the purification by column chromatography, a mixture of methanol and dichloromethane in a ratio of 1:1 is used and the salt formation is carried out with isopropyl alcohol containing 4 equivalents of hydrogen chloride.

Thus, 0.82 g (41.2%) of the title compound are obtained.

M.p.: 254–257° C.

Analysis: for $C_{22}H_{43}Cl_4N_7O_3S$ (627.51)

calculated: C, 42.11%; H, 6.91%; N, 15.62%; S, 5.11%; Cl, (ionic) 22.60%;

found: C, 42.75%; H, 6.85%; N, 15.38%; S, 5.26%; Cl, (ionic) 22.18%.

EXAMPLE 7

4,6-Diamino-2-[3-(4-formyl-1-piperazinyi) propylthio]-5-(2-ethoxybenzyl)pyrimidine A mixture of 3.14 g (10 mmoles) of 4,5-diamino-2-mercapto-5-(2-ethoxybenzyl)pyrimidine potassium salt, 2.76 g (20 mmoles) of potassium carbonate, 0.33 g (2 mmoles) of potassium iodide, 1.9 g (10 mmoles) of 1-formyl-4-(3-chloropropyl)piperazine and 30 ml of dimethylformamide is stirred at 80° C. for 9 hours. The inorganic compounds are removed by filtration, the filtrate is evaporated, and the product obtained is purified by chromatography over a column filled with Kieselgel 60 using a mixture of dichloromethane and methyl alcohol in a ratio of 8:1.

Thus, 1.83 g (42.5%) of the title compound are obtained.

M.p.: 154–156° C.

Analysis: for $C_{21}H_{30}N_6O_2S$ (430.58)

calculated: C, 58.58%; H, 7.02%; N, 19.52%; S, 7.45%;

found: C, 58.10%; H, 6.99%; N, 19.39%; S, 7.33%.

EXAMPLE 8

4,6-Diamino-2-[4-(4-methyl-1-piperazinyl) butylthio]-5-(2-methoxybenzyl)pyrimidine trihydrochloride hydrate A mixture of 2.6 g (8.6 moles) of 4,6-diamino-2-mercapto-5-(2-methoxybenzyl)pyrimidine potassium salt, 2.4 g (17 moles) of potassium carbonate, 0.15 g (0.9 mmoles) of potassium iodide, 2.26 g (8.6 mmoles) of 1-methyl4-(4-chlorobutyl)piperazine dihydrochloride and 40 ml of dimethylformamide is reacted at 140° C. for 20 hours as described in Example 7. The reaction mixture is worked up according to the procedure of Example 7, then the base obtained is dissolved in ethyl alcohol and reacted with isopropyl alcohol that contains 3 equivalents of hydrogen chloride.

Thus, 1.85 g (39.5%) of the title compound are obtained.

M.p.: 202° C.

Analysis: for $C_{21}H_{37}Cl_3N_6O_2S$ (543.99)

calculated: C, 46.37%; H, 6.86%; N, 15.45%; S, 5.89%; Cl, (ionic) 19.55%;

found: C, 46.82%; H, 6.82%; N, 15.38%; S, 5.74%; Cl (ionic) 19.35%.

EXAMPLE 9

4,6-Diamino-2-[3-(4-formyl-1-piperazinyl) propylthio]-5-(2-methoxybenzyl)pyrimidine A mixture of 3.94 g (13 mmoles) of 4,6-diamino-2-mercapto-5-(2-methoxybenzyl)pyrimidine potassium salt, 1.8 g (13 mmoles) of potassium carbonate, 0.22 g (1.3 mmoles) of potassium iodide, 2.5 g (13 mmoles) of 1-formyl-4-(3-chloropropyl)-piperazine and 50 ml of dimethylformamide is reacted for 7 hours in the manner described in Example 7. The product obtained after the evaporation step is crystallized from 150 ml of ice water, the crystals are filtered and dried.

Thus, 4.8 g (88.6%) of the title compound are obtained.

M.p.: 174–176° C.

Analysis: for $C_{20}H_{28}N_6O_2S$ (416.55)

calculated: C, 57.67%; H, 6.78%; N, 20.18%; S, 7.70;

found: C, 57.23%; H, 6.81%; N, 19.88%; S, 7.64%.

EXAMPLE 10

4,6-Diamino-2-[3-(1-piperazinyl)propylthio]-5-(2-methoxy-benzyl)pyrimidine trihydrochloride Method a)

To a suspension of 2.3 g (5.5 moles) of 4,6-diamino-2-[3-(4-formyl-1-piperazinyl)propylthio]-5-(2-methoxybenzyl)pyrimidine in 20 ml of ethyl alcohol, isopropanol containing 4 equivalents of hydrogen chloride are added, and the reaction mixture is boiled for 2.5 hours. After cooling, the solid matter is filtered and washed with diisopropyl ether.

Thus, 1.89 g (66.6%) of the title compound are obtained.

M.p.: 198° C.

Analysis: for $C_{19}H_{31}Cl_3N_6OS$ (497.92)

calculated: C, 45.83%; H, 6.28%; N, 16.88%; S, 6.44%; Cl, (ionic) 21.36%;

found: C, 45.41%; H, 6.34%; N, 16.38%; S, 6.33%; Cl, (ionic) 21.69%.

Method b)

A mixture of 3.0 g (10 mmoles) of 4,6-diamino-2-mercapto-5-(2-methoxybenzyl)pyrimidine potassium salt, 2.76 g (20 mmoles) of potassium carbonate, 0.33 g (2 mmoles) of potassium iodide, 2.36 g (10 mmoles) of 1-(3-chloropropyl)piperazine dihydrochloride and 30 ml of dimethylformamide is reacted for 5 hours in the manner described in Example 7. The product obtained after the evaporation step is crystallized from 120 ml of ice water, and the crude product is purified over a column containing Kieselgel 60. The eluent consists of a mixture of dichloromethane and methyl alcohol in a ratio of 8:2. The pure base obtained is dissolved in ethyl alcohol and reacted with isopropanol containing 3 equivalents of hydrogen chloride to obtain the trihydrochloride salt.

Thus, 2.1 g (42.2%) of the title compound are obtained.
M.p.: 197–198° C.
Analysis: for $C_{19}H_{31}Cl_3N_6OS$ (497.92)
calculated: C, 45.83%; H, 6.28%; N, 16.88%; S, 6.44%; Cl, (ionic) 21.36%;
found: C, 45.38%; H, 6.30%; N, 16.43%; S, 6.32%; Cl, (ionic) 21.30%.

EXAMPLE 11

4,6-Diamino-2-[2-(1-piperazinyl)ethylthio]-5-(2-butoxy-benzyl)pyrimidine trihydrochloride hydrate 0.25 g (11 mmoles) of sodium metal are dissolved in 50 ml of ethyl alcohol, then a solution of 3.6 g (10 mmoles) of 4,6-diamino-2-[2-(1-piperazinyl)ethylthio]-5-(2-hydroxybenzyl)-pyrimidine in 50 ml of ethyl alcohol is added. The reaction mixture is stirred for 20 minutes, then 1.37 g (10 mmoles) of n-butyl bromide are added, drop by drop, and the solution is stirred at the boiling point for 12 hours. The mixture is cooled, the inorganic salts are filtered, the filtrate is evaporated, and the crude product is purified by column chromatography over a column filled with Kieselgel 60 using a mixture of dichloromethane and methyl alcohol in a ratio of 8:2. The pure base obtained is dissolved in ethyl alcohol and reacted with isopropanol containing 3 equivalents of hydrogen chloride to obtain the trihydrochloride salt.

Thus, 2.54 g (45.2%) of the title compound are obtained.
M.p.: 180° C.
Analysis: for $C_{21}H_{39}Cl_3N_6O_3S$ (562.01)
calculated: C, 44.88%; H, 6.99%; N, 14.95%; S, 5.71%; Cl, (ionic) 18.92%;
found: C, 45.00%; H, 7.04%; N, 14.81%; S, 5.82%; Cl, (ionic) 18.76%.

EXAMPLE 12

4,6-Diamino-2-[3-(4-acetyl-1-piperazinyl)propylthio]-5-(2-methoxybenzyl)pyrimidine A mixture of 2.05 g (10 mmoles) of 1-acetyl-4-(3-chloropropyl)-piperazine, 2.85 g (9.5 mmoles) of 4,6-diamino-2-mercapto-5-(2-methoxybenzyl)pyrimidine potassium salt and 10 ml of ethyl alcohol is boiled for 2 hours. After cooling, the mixture is poured onto 40 ml of water, the product precipitated is filtered, washed with water, dried, and purified by chromatography over a column filled with Kieselgel 60 using a mixture of methanol and toluene in a ratio of 1:9. The crude product obtained is recrystallized from methyl alcohol.

Thus, 1.34 g (33.0%) of the title compound are obtained.
M.p.: 208–209° C.
Analysis: for $C_{21}H_{30}N_6O_2S$ (430.58%)
calculated: C, 58.58%; H, 7.02%; N, 19.52%; S, 7.45%;
found: C, 58.95%; H, 6.88%; N, 19.42%; S, 7.51%.

EXAMPLE 13

4,6-Diamino-2-[4-(4-methyl-1-piperazinyl)ethylthio]-5-(2-ethoxybenzyl)pyrimidine trihydrochloride hydrate 3.14 g (10 mmoles) of 4,6-diamino-2-mercapto-5-(2-ethoxybenzyl)pyrimidine potassium salt, 2.76 g (20 mmoles) of potassium carbonate, 0.33 g (2 mmoles) of potassium iodide and 2.36 g (10 mmoles) of 1-methyl-4-(2-chloroethyl)piperazine dihydrochloride are reacted in 25 ml of methyl alcohol as described in Example 3 for 28 hours. The product obtained after the evaporation is crystallized using ice water, then the crude product is subjected to chromatography over a column filled with Kieselgel 60 and using a mixture of dichloromethane and methyl alcohol in a ratio of 8:2. The pure base obtained is reacted with isopropanol containing 3 equivalents of hydrogen chloride to form the salt.

Thus, 1.93 g (36.4%) of the title compound are obtained.
M.p.: 121° C.
Analysis: for $C_{20}H_{35}Cl_3N_6O_2S$ (529.964)
calculated: C, 45.33%; H, 6.66%; N, 15.86%; S, 6.05%; Cl, (ionic) 20.07%;
found: C, 44.99%; H, 6.75%; N, 15.78%; S, 5.96%; Cl, (ionic) 19.57%.

EXAMPLE 14

4,6-Diamino-2-[3-(1-piperazinyl)ethylthio]-5-(2-ethoxybenzyl)-pyrimidine trihydrochloride trihydrate 4.73 g (15 mmoles) of 4,6-diamino-2-mercapto-5-(2-ethoxybenzyl)pyrimidine potassium salt, 2.08 g (15 mmoles) of potassium carbonate, 0.25 g (1.5 mmoles) of potassium iodide and 3.57 g (15 mmoles) of 1-(3-chloropropyl)-piperazine dihydrochloride are stirred in 50 ml of dimethylformamide at 120–125° C. for 20 hours. The reaction mixture is worked up as described in Example 7. The oil obtained is purified by chromatography over a column filled with Kieselgel 60 using a mixture of dichloromethane and methyl alcohol in a ratio of 8:2. The pure product obtained is reacted in ethanol with isopropanol containing 3 equivalents of hydrogen chloride to form the salt.

Thus, 3.92 g (46.17%) of the title compound are obtained.
M.p.: 116° C.
Analysis: for $C_{20}H_{39}Cl_3N_6O_4S$ (565.995)
calculated: C, 42.44%; H, 6.95%; N, 14.85%; S, 5.67%; Cl, (ionic) 18.79%;
found: C, 42.46%; H, 7.04%; N, 14.74%; S, 5.77%; Cl, (ionic) 19.60%.

EXAMPLE 15

4,6-Diamino-2-[3-(1-piperazinyl)propylthio]-5-(3,4,5-trimethoxybenzyl)pyrimidine trihydrochloride trihydrate 3.6 g (10 mmoles) of 4,6-diamino-2-mercapto-5-(3,4,5-trimethoxybenzyl)pyrimidine potassium salt, 2.76 g (20 mmoles) of potassium carbonate, 0.33 g (2 mmoles) of potassium iodide and 2.36 g (10 mmoles) of 1-(3-chloropropyl)piperazine dihydrochloride are stirred in 30 ml of dimethylformamide at 60–80° C. for 5 hours. The reaction mixture is worked up as described in Example 7. The oil obtained is purified by chromatography over a column filled with Kieselgel 60 using a mixture of dichloromethane and methyl alcohol in a ratio of 8:2. The pure product obtained is reacted in ethanol with isopropanol containing 3 equivalents of hydrogen chloride to form the salt.

Thus, 2.2 g (35.95%) of the title compound are obtained.

M.p.: 175° C.

Analysis: for $C_{21}H_{41}Cl_3N_6O_6S$ (612.021)

calculated: C, 41.21%; H, 6.75%; N, 13.73%; S, 5.24%; Cl, (ionic) 17.38%;

found: C, 41.99%; H, 6.72%; N, 13.78%; S, 5.44%; Cl, (ionic) 17.32%.

EXAMPLE 16

4,6-Diamino-2-[2-(4-acetyl-1-piperazinyl)ethylthio]-5-(2-methoxybenzyl)pyrimidine 2.22 g (10 mmoles) of 2-chloroethylpiperazine dihydrochloride are dissolved in 10 ml of water, the solution obtained is cooled to 0° C., an aqueous solution of 1.60 g (40 mmoles) of sodium hydroxide cooled to −5° C. is added, then, in a short time, 1.4 ml (1.57 g, 20 mmoles) of acetyl chloride are added, drop by drop, while maintaining the temperature below 5° C. The reaction mixture is stirred for further 5 minutes at this temperature, then extracted with ethyl acetate, and the organic phase is evaporated. The thus-obtained 1.64 g (86%, 8.6 mmoles) of 4-acetyl-1-(2-chloroethyl)piperazine are dissolved in 15 ml of ethanol. The solution obtained is boiled with 2.46 g (8.2 mmoles) of 4,6-diamino-5-(2-methoxybenzyl)-2-mercapto-pyrimidine potassium salt and 0.57 g (4.1 mmoles) of potassium carbonate for 2 hours, then poured onto 60 ml of water, filtered, and washed with water. The crude product obtained is recrystallized from methanol.

Thus, 1.70 g (50%) of the title compound are obtained.

M.p.: 198.5–199.5° C.

Analysis: for $C_{20}H_{28}N_6O_2S$ (416.55)

calculated: C, 57.67%; H, 6.78%; N, 20.18%; S, 7.70%;

found: C, 57.57%; H, 6.79%; N, 20.15%; S, 7.64%.

EXAMPLE 17

4,6-Diamino-2-[3-(1-piperazinyl)propylthio]-5-(4-chlorobenzyl)-pyrimidine trihydrochloride trihydrate 3.05 g (10 mmoles) of 4,6-diamino-2-mercapto-5-(4-chlorobenzyl)pyrimidine potassium salt, 2.76 g (20 mmoles) of potassium carbonate, 0.33 g (2 mmoles) of potassium iodide and 2.36 g (10 mmoles) of 1-(3-chloropropyl) piperazine dihydrochloride are stirred in 30 ml of dimethylformamide at 60 to 80° C. for 7 hours. The inorganic compounds are removed by filtration, the mother liquor is evaporated, and the residual oil is treated with water. The crystalline product obtained is subjected to chromatography over a column filled with Kieselgel 60 and using a mixture of dichloromethane and methyl alcohol in a ratio of 8:2. The pure product obtained is reacted in ethyl alcohol with isopropanol containing 3 equivalents of hydrogen chloride to form the salt.

Thus, 2.76 g (49.7%) of the title compound are obtained.

M.p.: 187° C.

Analysis: for $C_{18}H_{34}Cl_4N_6O_3S$ (556.39)

calculated: C, 38.86%; H, 6.16%; N, 15.10%; S, 5.76%; Cl, (total) 25.49%; Cl, (ionic) 19.12%;

found: C, 39.20%; H, 6.24%; N, 15.22%; S, 5.95%; Cl, (total) 25.77%; Cl, (ionic) 19.05%.

EXAMPLE 18

4,6-Diamino-2-[4-(1-piperazinyl)butylthio]-5-(2-methoxybenzyl)-pyrimidine trihydrochloride 3.0 g (10 mmoles) of 4,6-diamino-2-mercapto-5-(2-methoxybenzyl)pyrimidine potassium salt, 4.14 g (30 mmoles) of potassium carbonate, 0.33 g (2 mmoles) of potassium iodide and 2.5 g (10 mmoles) of 1-(4-chlorobutyl) piperazine dihydrochloride are stirred in 50 ml of dimethylformamide at 120 to 130° C. for 22 hours. The inorganic compounds are removed by filtration, and the crude product is purified as described in Example 17. The pure product is reacted with isopropanol containing 3 equivalents of hydrogen chloride to form the salt.

Thus, 2.38 g (46.6%) of the title compound are obtained.

M.p.: 255° C.

Analysis: for $C_{20}H_{33}Cl_3N_6OS$ (511.949)

calculated: C, 46.92%; H, 6.50%; N, 16.42%; S, 6.26%; Cl, (ionic) 20.78%;

found: C, 46.38%; H, 6.58%; N, 16.08%; S, 6.08%; Cl, (ionic) 20.31%.

EXAMPLE 19

4,6-Diamino-2-[2-(1-piperazinyl)ethylthio]-5-(4-fluorobenzyl)-pyrimidine trihydrochloride hydrate 2.88 g (10 mmoles) of 4,6-diamino-2-mercapto-5-(4-fluorobenzyl)pyrimidine potassium salt, 2.76 g (20 mmoles) of potassium carbonate, 0.33 g (2 mmoles) of potassium iodide and 2.22 g (10 mmoles) of 1-(2-chloroethyl) piperazine dihydrochloride are stirred in 30 ml of dimethylformamide at 60 to 80° C. for 6.5 hours. The inorganic compounds are removed by filtration, the mother liquor is evaporated, and the residue is subjected to chromatography over a column filled with Kieselgel 60 using a mixture of dichloromethane and methyl alcohol at a ratio of 8:2. The pure product obtained is reacted in ethyl alcohol with isopropanol containing 3 equivalents of hydrogen chloride to form the salt.

Thus, 1.81 g (36.94%) of the title compound are obtained.

M.p.: 168–170° C.

Analysis: for $C_{17}H_{28}Cl_3FN_6OS$ (489.874)

calculated: C, 41.68%; H, 5.76%; N, 17.16%; S, 6.55%; Cl, (ionic) 21.71%;

found: C, 41.72%; H, 5.79%; N, 17.26%; S, 6.49%; Cl, (ionic) 21.54%.

EXAMPLE 20

4,6-Diamino-2-[3-(1-piperazinyl)propylthio]-5-(4-fluorobenzyl)pyrimidine trihydrochloride hydrate To a solution of 5.6 g (100 mmoles) of potassium hydroxide in 140 ml of water, 5.76 g (20 mmoles) of 4,6-diamino-2-mercapto-5-(4-fluorobenzyl)pyrimidine potassium salt are added, and, to the stirred mixture, a solution of 4.71 g (20 mmoles) of 1-(3-chloropropyl)piperazine dihydrochloride in 20 ml of water are added, drop by drop. The reaction mixture is stirred at room temperature for 20 hours, the crystals precipitated are filtered, washed with water and dried. The product is subjected to chromatography over a column filled with Kieselgel 60 and using a mixture of dichloromethane and methyl alcohol in a ratio of 8:2. Then, the base obtained is reacted in ethyl alcohol with isopropanol containing 3 equivalents of hydrogen chloride to form the salt.

Thus, 6.6 g (65.5%) of the title compound are obtained.
M.p.: 269–271° C.
Analysis: for $C_{18}H_{30}Cl_3FN_6OS$ (503.901)
calculated: C, 42.91%; H, 6.0%; N, 16.68%; S, 6.36%; Cl, (ionic) 21.11%;
found: C, 42.74%; H, 6.07%; N, 16.36%; S, 6.28%; Cl, (ionic) 20.68%.

EXAMPLE 21

4,6-Diamino-2-{2-[4-(2-dimethylaminoethyl)-1-piperazinyl]-ethylthio}-5-(4-fluorobenzyi)pyrimidine tetrahydrochloride trihydrate To a solution of 2.6 g (48 mmoles) of potassium hydroxide in 50 ml of water, 2.31 g (8 mmoles) of 4,6-diamino-2-mercapto-5-(4-fluorobenzyl)pyrimidine potassium salt are added, and, to the mixture obtained, a solution of 2.78 g (8 mmoles) of 1-(2-chloroethyl)-4-(2-dimethylamino)piperazine trihydrochloride hydrate in 30 ml of water are added, drop by drop. The reaction mixture is stirred at room temperature for 8 hours, the crystals formed are filtered, washed with water. The base obtained is reacted in ethyl alcohol with isopropanol containing 3 equivalents of hydrogen chloride to form the salt.

Thus, 2.96 g (58.41%) of the title compound are obtained.
M.p.: 218–220° C.
Analysis: for $C_{21}H_{42}Cl_4FN_7O_3S$ (633.488)
calculated: C, 39.82%; H, 6.68%; N, 15.48%; S, 5.06%; Cl, (ionic) 23.39%;
found: C, 39.84%; H, 6.50%; N, 15.59%; S, 5.19%; Cl, (ionic) 22.69%.

EXAMPLE 22

4,6-Diamino-2-[3-(1-piperazinyl)propylthio]-5-(4-methoxybenzyl)-pyrimidine trihydrochloride dihydrate 3.0 g (10 mmoles) of 4,6-diamino-2-mercapto-5-(4-methoxybenzyl)pyrimidine potassium salt, 2.76 g (20 mmoles) of potassium carbonate, 0.33 g (2 mmoles) of potassium iodide and 2.36 g (10 mmoles) of 1-(3-chloropropyl)piperazine dihydrochloride are reacted in 30 ml of dimethylformamide at 60 to 80° C. for 8 hours. Then the procedure of Example 17 is followed.

Thus, 2.6 g (48.7%) of the title compound are obtained.
M.p.: 110–113° C.
Analysis: for $C_{19}H_{35}Cl_3N_6O_3S$ (533.95)
calculated: C, 42.74%; H, 6.61%; N, 15.74%; S, 6.01%; Cl, (ionic) 19.92%;
found: C, 42.25%; H, 6.72%; N, 15.38%; S, 5.95%; Cl, (ionic) 19.27%.

EXAMPLE 23

4,6-Diamino-2-[2-(1-piperazinyl)ethylthio]-5-(4-methoxybenzyl)-pyrimidine hydrate 3.0 g (10 mmoles) of 4,6-diamino-3-mercapto-5-(4-methoxybenzyl)pyrimidine potassium salt, 2.76 g (20 mmoles) of potassium carbonate, 0.33 g (2 mmoles) of potassium iodide and 2.22 g (10 mmoles) of 1-(2-chloroethyl)piperazine dihydrochloride are reacted in 30 ml of dimethylformamide at 80° C. for 14 hours. The organic compounds are removed by filtration, the mother liquor is evaporated, and the residue is subjected to chromatography over a column filled with Kieselgel 60 using a mixture of dichloromethane and methyl alcohol in a ratio of 8:2.

Thus, 2.03 g (51.72%) of the title compound are obtained.
M.p.: 135–136° C.
Analysis: for $C_{18}H_{28}N_6O_2S$ (392.527)
calculated: C, 55.08%; H, 7.19%; N, 21.41%; S, 8.17%;
found: C, 54.86%; H, 7.17%; N, 21.11%; S, 8.11%.

EXAMPLE 24

4,6-Diamino-2-[3-(1-piperazinyl)propylthio]-5-(4-dimethylaminobenzyl)-pyrimidine tetrahydrochloride trihydrate 3.13 g (10 mmoles) of 4,6-diamino-2-mercapto-5-(4-dimethylaminobenzyl)pyrimidine potassium salt, 2.76 g (20 mmoles) of potassium carbonate, 0.33 g (2 mmoles) of potassium iodide and 2.36 g (10 mmoles) of 1-(3-chloropropyl)piperazine dihydrochloride are boiled in 50 ml of methyl alcohol for 5 hours. The inorganic compounds are removed by filtration, the mother liquor is evaporated, and the residue is subjected to chromatography over a column filled with Kieselgel 60 using a mixture of dichloromethane and methyl alcohol in a ratio of 8:2. The base obtained is reacted in ethyl alcohol with isopropanol containing 3 equivalents of hydrogen chloride to form the salt.

Thus, 2.65 g (44.06%) of the title compound are obtained.
M.p.: 120–124° C.
Analysis: for $C_{20}H_{41}Cl_4N_7O_3S$ (601.47)
calculated: C, 39.94%; H, 6.87%; N, 16.30%; S, 5.33%; Cl, (ionic) 23.58%;
found: C, 40.32%; H, 6.82%; N, 15.85%; S, 5.45%; Cl, (ionic) 23.16%.

EXAMPLE 25

4,6-Diamino-2-[2-(1-piperazinyl)ethylthio]-5-(4-isopropylbenzyl)-pyrimidine 2.0 g (7 mmoles) of 4,6-diamino-2-mercapto-5-(4-isopropylbenzyl)pyrimidine, 2.9 g (28 mmoles) of potassium carbonate, 0.33 g (2 mmoles) of potassium iodide and 1.7 g (7 mmoles) of 1-(2-chloroethyl)piperazine dihydrochloride are reacted in 30 ml of dimethylformamide at 60 to 80° C. for 5 hours. The inorganic compounds are removed by filtration, the mother liquor is evaporated, and the residue is subjected to chromatography over a column filled with Kieselgel 60 using a mixture of dichloromethane and methyl alcohol in a ratio of 8:2.

Thus, 1.56 g (57.65%) of the title compound are obtained.
M.p.: 63–64° C.
Analysis: for $C_{20}H_{30}N_6S$ (386.655)
calculated: C, 62.14%; H, 7.82%; N, 21.74%; S, 8.29%;
found: C, 61.94%; H, 7.75%; N, 21.38%; S, 8.15%.

EXAMPLE 26

4,6-Diamino-2-{2-[4-(3-dimethylaminopropyl)-1-piperazinyl]-ethylthio}-5-(2-methoxybenzyl)pyrimidine tetrahydrochloride hydrate To a solution of 3.37 g (60 mmoles) of potassium hydroxide in 60 ml of water, 3.0 g (10 mmoles) of 4,6-diamino- 2-mercapto-5-(2-methoxybenzyl)pyrimidine potassium salt are added, and, to the stirred mixture, a solution of 3.61 g (10 mmoles) of 1-(2-chloroethyl)-4-(3-dimethylaminopropyl)piperazine trihydrochloride hydrate in 30 ml of water are added, drop by drop. The reaction mixture is stirred at room temperature for 30 hours, the crystals formed are filtered, washed with water. The base is reacted in ethyl alcohol with isopropanol containing 4 equivalents of hydrogen chloride to form the salt.

Thus, 3.31 g of the title compound are obtained.

M.p.: 262–264° C.

Analysis: for $C_{23}H_{43}Cl_4N_7O_2S$ (623.521)

calculated: C, 44.31%; H, 6.95%; N, 15.72%; S, 5.14%; Cl, (ionic) 22.74%;

found: C, 44.21%; H, 6.90%; N, 15.19%; S, 5.05%; Cl, (ionic) 22.17%.

What is claimed is:

1. A compound of formula (I):

where $R^1$ is selected from the group consisting of hydrogen, $C_{1-4}$ alkyl, $C_{1-4}$ alkanoyl, and di($C_{1-4}$ alkyl)amino($C_{1-4}$ alkyl);

$R^2$ is selected from the group consisting of hydrogen and benzyl substituted with 1 to 3 substituents selected from the group consisting of $C_{1-4}$ alkyl, $C_{1-4}$ alkoxy, di($C_{1-4}$ alkyl)amino, hydroxy, and halo; and n is 2, 3, or 4, or a pharmaceutically acceptable acid addition salt thereof.

2. A compound of claim 1 where $R^1$ is selected from the group consisting of hydrogen, $C_{1-4}$ alkyl, $C_{1-4}$ alkanoyl, and di($C_{1-4}$ alkyl)aminoethyl.

3. A compound of claim 1 where $R^1$ is selected from the group consisting of hydrogen, $C_{1-4}$ alkanoyl, and dimethylamino($C_{1-4}$ alkyl); and n is 2 or 3.

4. A compound of claim 3 where $R^1$ is selected from the group consisting of hydrogen and dimethylamino($C_{1-4}$ alkyl);

$R^2$ is benzyl substituted with $C_{1-4}$ alkoxy or fluoro; and n is 2.

5. A process for the preparation of a compound of formula (I):

where $R^1$, $R^2$, and n are as defined in claim 1, or a pharmaceutically acceptable acid addition salt thereof, comprising:

(a) reacting a compound of formula (II):

where $R^2$ is as defined above, or an alkali metal salt thereof, with a compound of formula III:

where $R^2$ and n are as defined above; and

Hlg is halo, or an acid addition salt thereof, to form the compound of formula (I), or an acid addition salt thereof; and, optionally (b) converting the compound of formula (I) to a pharmaceutically acceptable acid addition salt thereof, or liberating the compound of formula (I) from the acid addition salt thereof.

6. The process of claim 5 where Hlg is chloro or bromo.

7. A pharmaceutical composition comprising a compound of claim 1 and at least one carrier.

8. A pharmaceutical composition comprising a compound of claim 2 and at least one carrier.

9. A pharmaceutical composition comprising a compound of claim 3 and at least one carrier.

10. A pharmaceutical composition comprising a compound of claim 4 and at least one carrier.

11. A method of treating a patient suffering from a central nervous system disorder, comprising administering to the patient a therapeutically effective amount of a compound of claim 1.

12. The method of claim 11 where the central nervous system disorder is anxiety.

13. A method of treating a patient suffering from a central nervous system disorder, comprising administering to the patient a therapeutically effective amount of a compound of claim 2.

14. The method of claim 13 where the central nervous system disorder is anxiety.

15. A method of treating a patient suffering from a central nervous system disorder, comprising administering to the patient a therapeutically effective amount of a compound of claim 3.

16. The method of claim 15 where the central nervous system disorder is anxiety.

17. A method of treating a patient suffering from a central nervous system disorder, comprising administering to the patient a therapeutically effective amount of a compound of claim 4.

18. The method of claim 17 where the central nervous system disorder is anxiety.

* * * * *